United States Patent [19]

Hauck et al.

[11] 4,399,550
[45] Aug. 16, 1983

[54] SPINNING FILTER FOR X-RAY APPARATUS

[75] Inventors: Robert B. Hauck, Delafield; Floyd L. Gray, Hales Corners; Richard T. Brandt, New Berlin, all of Wis.

[73] Assignee: General Electric Company, Schenectady, N.Y.

[21] Appl. No.: 238,910

[22] Filed: Feb. 27, 1981

[51] Int. Cl.³ .............................................. G21K 3/00
[52] U.S. Cl. ........................................ 378/5; 378/157
[58] Field of Search ..................... 378/156, 157, 5, 16, 378/106

[56] References Cited
U.S. PATENT DOCUMENTS

4,029,963  6/1977  Alvarez ................................. 378/5
4,277,685  7/1981  Covic ................................. 378/150

Primary Examiner—Craig E. Church
Attorney, Agent, or Firm—Ralph G. Hohenfeldt

[57] ABSTRACT

Curved X-ray filter elements are arranged circularly around a drum. Alternate circumferentially adjacent elements have different filtration properties. Diametrically opposite elements have the same properties. An X-ray source provides a sequence of alternate low and high energy X-ray beam pulses. A multicell X-ray detector produces X-ray attenuation data for each pulse and the data is switched to alternate memories. A drum drive motor is energized at power line frequency. A pinion on the motor shaft turns a gear. A lug that is mounted for angular adjustment on the gear drives the drum. A multiple blade shutter is also mounted on the gear for angular adjustment and rotation with the gear. The shutter alternately interrupts and restores a light beam to a photosensitive device which produces corresponding signal state changes or trigger signals. The signals are used to synchronize the low and high energy X-ray pulses, the filter element angular locations and memory switching with power line frequency.

11 Claims, 8 Drawing Figures

SPINNING FILTER FOR X-RAY APPARATUS

BACKGROUND OF THE INVENTION

This invention relates to a filter device for use in diagnostic X-ray systems. The new filter device is applicable to various X-ray systems but will be illustrated in connection with a computed projection radiography system.

A computed projection radiography (CPR) system produces conventional radiographic type images using a computer to process the X-ray attenuation data for the images instead of using a film. In the CPR method, a thin fan-shaped beam of X-rays is formed. Typically, the beam is collimated to a thickness in the range of 1.5 to 2.0 mm. The beam is pulsed on and off at a rate of typically 60 times per second. The patient being examined is moved in linear increments in a longitudinal direction that is perpendicular to the plane of the pulsed fan-shaped X-ray beam. A multicell X-ray detector is located for intercepting the thin differentially attenuated X-ray beam as it emerges from the body. The detector cells each intercept a small bundle of rays and each produces an analog signal representative of the X-ray beam attenuation along its ray path through the body for each X-ray pulse. The analog attenuation data obtained during each pulse from each body slice or view is subjected to an appropriate algorithm in a computer that yields pixel signals which, when assembled in an array corresponding with the width and length of the body portion that has been scanned can be used to reconstruct a two-dimensional radiographic image for display on a television monitor, for example. It should be noted that the body can be moved through the beam or the beam can be scanned over the body.

Use of a thin X-ray beam as in CPR reduces the effects of radiation scattering within the body so image resolution is improved. In ordinary projection radiography where the image is recorded on film and the X-ray beam is divergent in orthogonal directions and wide enough to cover the entire field of view at one time, radiation is scattered by volume elements in the body from one ray path to another or, in other words, it is scattered from substantially any part of the field to all other parts of the field. This results in less than optimum image contrast and resolution.

The more advanced CPR system in which the new filter device disclosed herein will be illustrated provides at least a pair of X-ray pulses for each slice or longitudinal increment of the body being scanned. One X-ray pulse in a pair has higher energy than that of the other. The second pulse in a pair can start just as soon as the first one ends so that both pulse beams pass through the same slice of the body. The bouble pulse scan is continued over the anatomical region of interest. A separate set of attenuation data for each slice of the body, that is, for each high and low energy X-ray pulse is acquired on a line-by-line basis and the data for the pulses are switched to different memories as they are acquired for being processed by the computer. This would permit reconstruction of two images which are substantially spatially coincident. After the computer reconstructs the images they could be displayed individually. Usually, however, the picture element data for the two independent images is weighted and then the data for one image is subtracted from the other to produce a matrix of picture element data that results in a displayed image wherein anatomy that is obscured in the individual images is easily visualized. The data for the individual images can also be processed by the computer to produce edge enhancement, noise suppression, gamma correction and accomplish window and level control of intensities that are not otherwise achievable with radiographic film.

As is known, for performing subtraction CPR, it would be desirable for the low and high energy beams to be monoenergetic or fall within very narrow spectral bands. However, when a particular high or low kilovoltage is applied between the anode and cathode of the X-ray tube the resulting X-ray beam will be comprised of photons having a distribution of energies. The customary way of narrowing the spectral band is to insert filter elements in the X-ray beam. Thus, for subtraction CPR, during the high energy X-ray beam pulse, a filter that removes photons having an energy significantly below the selected high energy is inserted in the beam. During the low energy pulse, the filter that takes out photons having an energy above a predetermined level is inserted in the beam.

Figure 2:
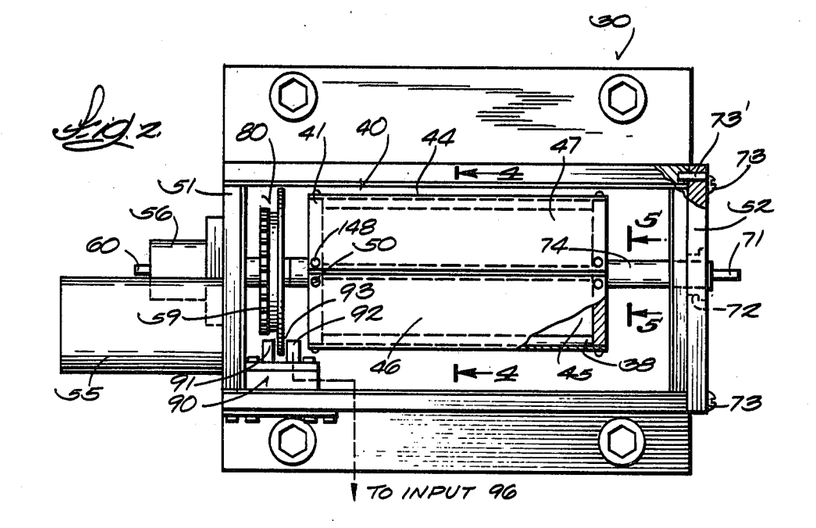
FIG. 2 is a bottom plan view of the filter device.

The concept of obtaining X-ray beams at different energy levels by rotating two different kinds of filters across the path of a polyenergetic X-ray beam, rather than successive beams at different energies, so that beams of different spectral bands can be obtained in close succession is known in the prior art. U.S. Pat. No. 4,029,963, particularly in FIG. 2, illustrates a rotating filter device comprising a disk having diametrically opposite apertures in which filters that pass different spectral bands are located. The system uses the X-ray detector output to trigger the switch which directs data corresponding to the different X-ray energies to different memories. A disadvantage of this is that signals at one energy level are still persisting while signals at the other energy level have begun to occur or are about to begin occurring. Little if any time is available for the detector elements to deionize or clear. The system is not appropriate for the preferred case where the X-ray tube itself is pulsed at two different voltage levels as in the CPR system described herein. In addition, with prior art filter devices it would be difficult, if not impossible, to have a X-ray pulses occur when the respective filters are in the identical angular position during each revolution.

SUMMARY OF THE INVENTION

The illustrative embodiment of the new filter device disposes different filter elements, in the form of segments of a cylinder on a hollow drum, in the fan-shaped X-ray beam paths. Diametrically opposite filter segments are of the same material. In the dual X-ray pulse system illustrated herein, 90° of drum rotation disposes a different pair of diametrically opposite filter elements in the X-ray beam. The low and high energy X-ray pulses are caused to occur in synchronism while corresponding filter element pairs are in the same angular position for every half revolution. In other words, each filter element pair is in the X-ray beam path twice for each drum revolution. The filter drum is driven with an ac motor whose speed depends on power line frequency. In the illustrated embodiment, there is a pinion on the shaft of the motor which drives a gear. A double-bladed shutter wheel is mounted on the gear and is adjustable on the gear about its rotational axis. A hub or coupling element for driving the cylinder is also mounted on the gear for being adjusted or set at a selected angle. The rotating shutter interrupts a light beam to an optical sensor whose output changes state as the consecutive angular positions of the shutter blades occur. The state changes or output signal level changes are used to trigger the X-ray source to produce the closely occurring low and high energy pulses in a pair and used to synchronously switch data between memories. Independent angular adjustment of the shutter and of the lug or drum driving element enables having X-ray pulses occur when the filter elements are in identical rotational positions and, furthermore, it permits having the X-ray pulses occur at any selected point and at the same point in the sinusoidal line frequency waveform. The shutter acts as a commutator for switching the high and low energy X-ray pulses on and off at the proper times. Looking at it another way, providing for adjusting the shutter and drive hub enables accounting for the phase shift of the ac motor relative to power line frequency that is caused by the mechanical load imposed on the motor.

Another feature is to provide feedback to the X-ray tube trigger electronics to detect the position of the filter assembly and provide a signal to initiate pulsing of the X-ray tube.

How the foregoing various objects of the invention are achieved will be evident in the ensuing more detailed description of a preferred embodiment of the new filter device which will now be set forth in reference to the drawings.

DESCRIPTION OF A PREFERRED EMBODIMENT

Figure 1:
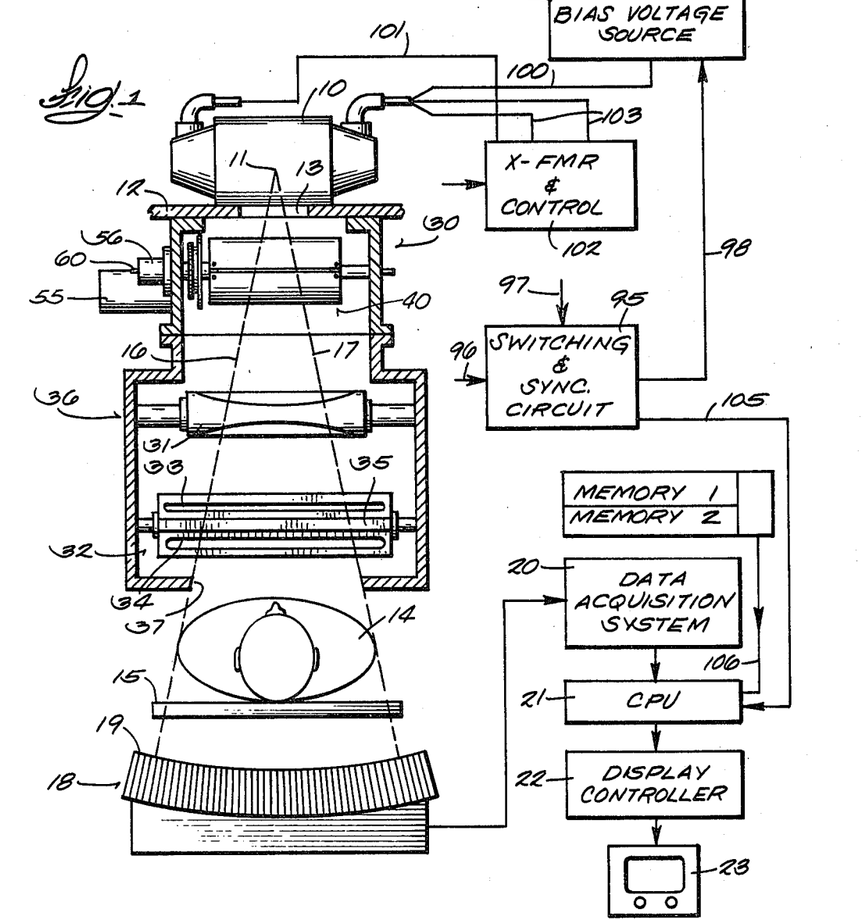
FIG. 1 is a diagram of a computed projection radiography system in which the new filter device is used.

The computed projection radiography (CPR) system depicted in FIG. 1 comprises a casing 10 that contains an X-ray tube which is not visible. However, the focal spot on the X-ray tube target from which the X-ray beam emanates may be considered to be at the point marked 11. The X-ray tube casing is mounted on a plate member 12 which has a long narrow slot 13 through which the X-ray beam pulses are projected toward a patient 14 who is supported on an X-ray transmissive table top 15. In the CPR system depicted in FIG. 1, the X-ray beam has a thin cross-section and diverges from focal spot 11 toward the patient 14. The boundaries of the diverging or fan-shaped beam are indicated by the dashed lines marked 16 and 17. Thus, the lower and higher energy X-ray beam pulses in a pair pass through the same layer or slice of the patient.

When the differentially attenuated beam emerges from the patient, it is received in a known type of multi-cell X-ray detector which is generally designated by the numeral 18. The detector is comprised of a plurality of juxtaposed cells such as the one marked 19. Each cell intercepts a bundle of the rays which comprise the X-ray beam at each energy after the beam has emerged from the body. The cells produce analog signals corresponding in magnitude to the amounts by which the ray bundles have been differentially attenuated by passing through the body.

Using the apparatus diagrammed in FIG. 1 to perform the computed radiography subtraction process involves moving the patient 14 longitudinally and perpendicularly to the plane of the fan-shaped X-ray beam in a step-by-step fashion. For each increment of movement the X-ray source is turned on and off or pulsed twice. One pulse in a pair has lower X-ray or photon energy than the other. For instance, for one pulse about 140 kilovolts-peak (kVp) may be applied between the anode and cathode of the X-ray tube to produce an X-ray beam whose peak photon energy corresponds to about 140 kilovolts. The other X-ray pulse energy may correspond to about 70 kVp. The width of the X-ray pulses is about 5 ms by way of example and not limitation. The low and high energy X-ray pulses in a pair occur in very close succession to each other. For example, a low energy X-ray pulse is produced during one cycle of the sinusoidal ac power line waveform and a high energy pulse in a pair is produced during the next cycle. Thus, if power line frequency is 60 Hz, there is a 16.6 ms window available for each X-ray pulse.

The patient is scanned or advanced through the beam until the anatomical region of interest has been scanned. X-ray image projections are thereby obtained on a line-by-line basis. A discrete set of attenuation data signals is produced by the plurality of cells comprising detector 18 for each high and low energy X-ray pulse coincident with a slice of the patient. In other words, data for producing projection images of a single slice of the body is produced by each pair of pulses. The analog attenuation data for each slice is received by a data acquisition system, indicated by the block marked 20, wherein the signals may be amplified and converted to corresponding digital signals which are multiplexed to a computer that is represented by the block marked 21 and labelled CPU. The CPU executes algorithms which results in production of a matrix of digital signals representative of picture elements (pixels) for the composite images made up of the scan lines. A separate set of picture element signals are produced for the high and low energy images. Thus, the CPU can weigh and subtract the data representative of the image obtained with the low energy pulses from the image obtained with the high energy pulses. The resulting signals may be transmitted to a display controller which is symbolized by the block marked 22. The display controller converts the digital pixel signals to analog video signals which drive a television monitor 23 that displays the image resulting from subtraction of the high and low energy X-ray images.

Referring to FIG. 1, the X-ray beam originating at focal spot 11 passes through an elongated slot 13 and then through the new rotating filter device which is designated generally by the reference numeral 30. This device will be described in detail later.

After passing through filter device 30, the X-ray beam passes through another filter 31 which is in an X-ray impermeable housing 36. Filter 31 is commonly known as a bow-tie filter because of its configuration. It is thicker at its ends than at its center and is designed to equalize the X-ray beam intensity across the width of the beam to compensate for the fact that the body is thicker in its mid region that at its sides. Filter 31 is composed of a material whose X-ray attenuation properties at a range of X-ray tube anode kilovoltages approximates that of water. Acrylic resin is one material that has been commonly used.

After passing through filter 31, the X-ray beam passes through a beam thickness defining collimator which is generally designated by the numeral 32 and is also enclosed in housing 36. Collimator 32 is cruciform in cross-section such as to define four radially extending blades in the illustrative device. Each blade has an axially extending slot such as the slots marked 33 and 34. Each slot has a different width to permit defining one of four beam thicknesses in this particular case. As shown, the X-ray beam is passing through a slot in a collimator blade marked 35. The cruciform collimator is, of course, rotatable to enable selection of the desired slot size and, hence, the thickness of the fan-shaped high and low energy beams. For CPR, the fan-shaped X-ray beam is usually collimated down to a thickness of under 1 cm. Thus, it is appropriate to translate the body longitudinally and perpendicularly to the plane of the fan-shaped beam in one centimeter increments. During each increment of longitudinal body movement, at least one high energy and one low energy X-ray pulse is produced. The X-ray pulses in a pair are so close in time that the stop motion effect is obtained. Typically, the durations of the low and high energy pulses will be in the range of 1 to 5 ms. The width of the fan-shaped X-ray beam is defined by the end edges of a transversely extending slot or beam exit aperture 37 in the bottom of housing 36.

The new spinning filter which has been generally designated by the numeral 30 will now be described in greater detail in reference to FIGS. 2–8.

Figure 4:
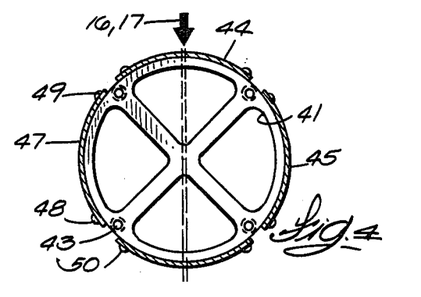
FIG. 4 is a transverse section of the filter drum taken on a line corresponding with 4—4 in FIG. 2.

A plan view of the spinning filter drum is depicted in FIG. 2 where it is generally designated by the numeral 40 and is inside of filter housing 30. A transverse section through the drum is shown in FIG. 4. The filter drum 40 has spoked rings 41 and 42 at its opposite ends. These rings are connected together to form a drum by means of four rods such as the one marked 38. The rods are spaced ninety degrees apart around the periphery of the end rings and the space between the rods can be considered windows through which the fan-shaped X-ray beams can pass. The center of the drum is, of course, clear of anything that could absorb X-radiation except air. The axially extending rods, such as the one marked 38, are secured to the spoked rings 41 and 42 by means of screws in their ends which can be seen clearly in FIGS. 4 and 5 where one of the screws is marked 43.

Figure 5:
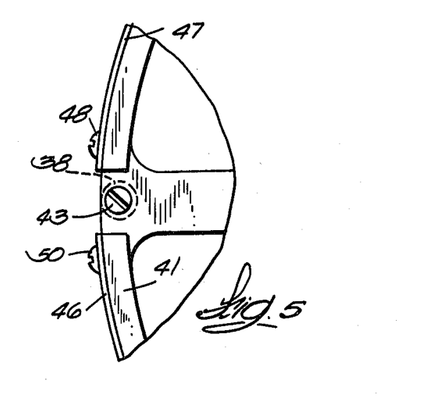
FIG. 5 shows a fragment of the end of the filter drum looking in the direction of the arrows 5—5 in FIG. 2.

As can be seen particularly well in FIGS. 4 and 5, there are four curved filter elements 44–47 extending axially between the rings 41 and 42 concentrically with them. The filter elements are fastened to the wheels by means of screws such as those marked 48–50 in FIG. 4. For the skae of clarity, the section of the drum shown in FIG. 4 is rotated forty-five degrees relative to the rotational position in which it is shown in FIGS. 2 and 5. In FIG. 4, diametrically opposite curved filter elements 44 and 46 are made of the same material. Diametrically opposite filter elements 45 and 47 are also made of the same material but of a different material than the filter elements 44 and 46. For instance, in a case where the high energy X-ray pulses corresponded to about 140 kVp and the low energy pulses to about 70 kVp, phosphor bronze was used for filter element pair 44 and 46 and erbium was used for element pair 45 and 47. The phosphor bronze filter elements were in the X-ray beam during high energy X-ray pulses and the erbium elements were in the beam during the low energy X-ray pulses.

As shown in FIG. 4, the thin fan-shaped X-ray beam 16, 17 is projected through similar diametrically opposite filter elements 44 and 46 when the drum is in the rotational position depicted in FIG. 4. Another 90° of rotation will put diametrically opposite filter elements 45 and 47 in the beam. In other words, a different pair of filter elements is disposed in the X-ray beams for every 90° of drum rotation. As can be seen, for every full revolution of the drum each pair of diametrically opposite filter elements will be in the X-ray beam twice. Of course, for one high energy X-ray pulse filter element 44 will be on top and similar element 46 will be on the bottom so the beam will pass through both diametrically opposite elements. During the next high energy X-ray pulse, filter element 46 will be on top and 44 will be on the bottom but the beam will still pass through the same amount of filter material and, in accordance with the invention, through the same place during each pulse. The same is true of the other pair of filters which are in the beam during the low energy pulses. As will be evident when the drive system for the filter drum is described, a feature of the invention is to have the filter drum in the same angular position each time the low and high energy X-ray pulses occur. This assures that every X-ray pulse will be filtered by the same amount even if there should happen to be small differences in the filter properties from one zone to another in the individual filter elements. In some applications the one diametrically opposite pair of filter elements might be omitted in which case air would constitute the filtration or lack of it for a beam at one energy or the other. As will be explained shortly hereinafter, the drive system for the filter drum enables synchronizing occurrence of the high and low energy X-ray pulses and the constant rotational positions of the filter elements with power line frequency.

Figure 3:
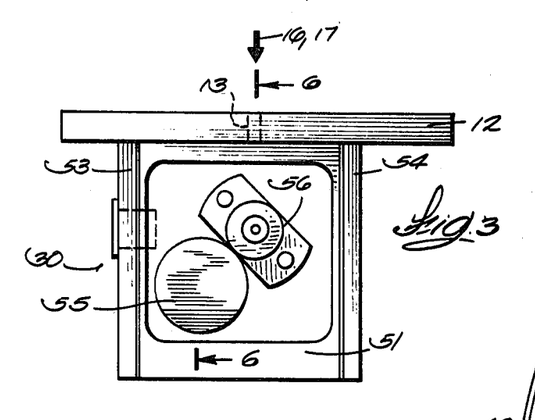
FIG. 3 is an end elevation view of the filter device.

The filter drum drive and power line frequency synchronizing drive mechanism will now be described primarily in reference to FIGS. 2, 3, 6 and 7. FIG. 3 shows a left end elevation of the housing 30 of spinning filter drum unit 40. The housing has end walls 51 and 52 and side walls 53 and 54. As can be seen in FIGS. 3 and 2, the bottom of the housing is open. The walls of the housing are mounted to plate 12 which has the elongated slot 13 that accomplishes the preliminary collimation of the X-ray beam before it passes through the filter elements on the rotation drum. An ac motor 55 is mounted to end wall 51 of the rotating filter housing end wall 51. A bearing block 56 is also mounted to wall 51. Motor 55 is operated at power line frequency such as 60 Hz. In the illustrative embodiment, a two-pole motor is used so it rotates at 3600 rpm although its rotor will be shifted in phase in relation to power line frequency because of the mechanical loading.

Figure 6:
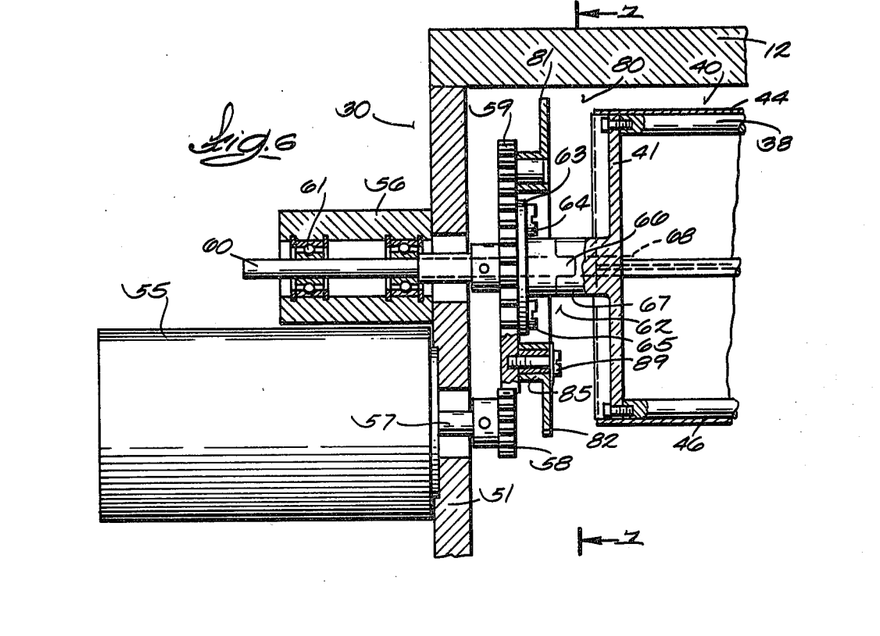
FIG. 6 is a partial side elevation view, partially in section, of the filter device.

As can be seen in FIG. 6, the shaft 57 of constant speed motor 55 extends through end housing wall 51 and has a pinion 58 fastened to it. The pinion drives a gear 59 which is fastened to a shaft 60. The shaft is journaled for rotation in ball bearings such as the one marked 61 which are in the housing or bearing block 56. In this illustration, the ratio between driven gear 59 and driving pinion 58 is 4:1. Thus, when motor 55 is turning at 3600 rpm, gear 59 will turn at 900 rpm in this illustrative embodiment of the invention.

Gear 59 has a drive lug device 62 fastened to one of its faces. The drive lug is a unitary element comprised of a flange 63 that is clamped to gear 59 by means of a pair of screws 64 and 65. As can be seen in FIG. 6, the drive lug has a diametrically extending tongue 66 projecting axially from its end. The tongue extends into the end of a hub 67 which is integral with end ring 41 of the drum assembly. It will be evident that when the gear 59 is driven, lug 62 will turn and cause rotation of the filter drum 40 to which it is coupled. Shaft 60 passes through drive lug 62 and drum hub 67 with a small clearance. The end 68 of shaft 60 extends into the filter drum for a short distance to provide support for the drum and to prevent the driven grooved drum hub 67 from falling off of tongue 66 of the driving hub 62 when the drum is rotating.

Figure 7:
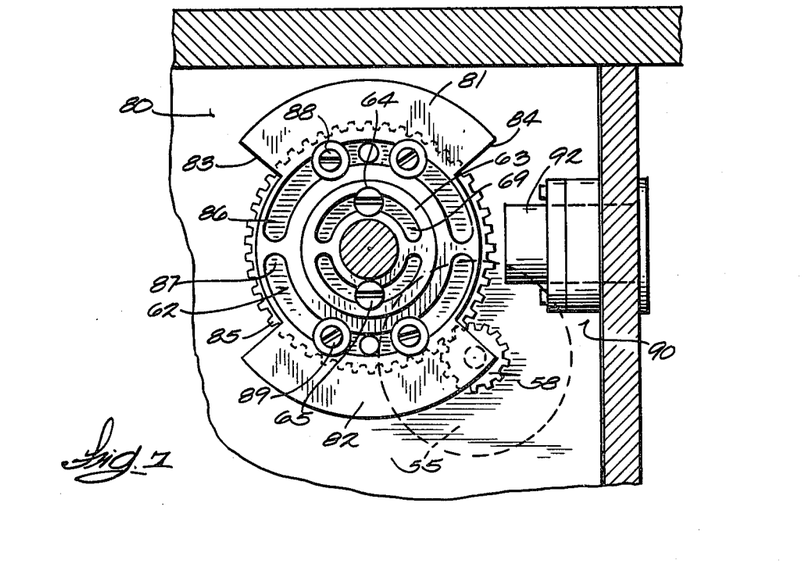
FIG. 7 is a section taken on a line corresponding with 7—7 in FIG. 6.

As can be seen in FIG. 7, the drive lug flange 63 has a pair of substantially semicircular slots 69 and 70 through which the thread shanks of the clamping screws 64 and 65 extend. Slots 69 and 70 permit the rotational angle of the drive lug relative to the motor shaft to be adjusted to account for any amount of phase angle shift from power line current which might exist. The object of the drive lug adjustment and/or shutter adjustment (to be described) is to establish the filter drum at the same angular position relative to power line frequency for every X-ray pulse. Moreover, this permits controlling the X-ray pulses to occur at any selected location along the sinusoidal power line frequency waveform as will be disucssed in more detail later.

At this time it may be noted that changing filter drums is convenient in the illustrated filter device. As can be seen in FIG. 2, the outboard end of the filter drum remote from the driven end has a shaft 71 fixed in it that is journaled in a ball bearing 72. Bearing 72 is mounted in end wall 52 which is made removable by reason of it being secured to the side walls of the filter housing with screws such as the one marked 73 and dowel pins 73' which assure that the end wall is accurately and reproducibly located. There is a spacer sleeve 74 fitted on shaft 71 to maintain the filter drum in a constant axial position. To change the filter drum or to simply substitute pairs of filter elements having different attenuation properties on the drum, it is only necessary to remove screws 73 and then back the filter drum assembly 40 out of the housing on the separable wall 52. Using the lug 66 to drive the cylinder also facilitates detachment of the driven cylinder hub 67 from the driving lug tongue 66 in connection with filter drum exchange.

A shutter that interrupts a light beam to a photosensitive device to produce filter rotational position indicating signals is used for controlling the angle along the sinusoidal power line waveform at which the X-ray pulses occur. The shutter is designated generally by the reference numeral 80. As can be seen in FIGS. 6 and 7, shutter 80 is fastened to gear 59 concentrically with the drive hub flange 63. The configuration of shutter 80 can be seen in FIG. 7. It comprises two diametrically opposite radially extending opaque circular segments or blades 81 and 82. There are diametrically opposite circular gaps 83 and 84 between shutter blades 81 and 82. As shown in FIG. 6, the blades 81 and 82 extend from a central cylindrical portion 85 of the shutter. As shown in FIG. 7, the front face of the shutter is provided with a pair of substantially semicircular holes or slots 86 and 87 through which opposite pairs of headed clamping screws, such as those marked 88 and 89, extend. Clamping screws 88 and 89 permit the shutter to be adjusted rotationally on gear 59 about its rotational axis. Thus, the drive hub 62 and the shutter 80 are both adjustable around the axis of gear 59.

In a commercial embodiment, the opaque shutter blade segment 81 and 82 span an angle of about 99° and the gap 83 and 84 between the blades span about 81°.

Shutter 80 is adapted to interrupt a light beam leading to a photosensitive device for providing switching signals indicative of the angular position or phase of the shutter relative to power line frequency. A commercially available light source and photosensitive device assembly 90 cooperates with the shutter as can be seen in FIG. 2. Assembly 90 has two spaced apart members 91 and 92 which provide a gap 93 through which the rotating shutter blade circular segments and gaps transit. Member 91 contains a light source, not visible, that projects its beam across gap 93 to member 92 which contains a photosensitive device, such as a photodiode, not visible. The output signal from the photodiode changes state every time a rotating shutter blade initiates interruption of the light beam and every time the light beam is restored by passing through the gaps between the shutter blades. Thus, in the illustrated embodiment, there are four signal state changes for every complete revolution of the two-blade and two-gap shutter blade assembly. The reason, in the illustrative embodiment, for having the shutter blades and shutter gaps at an unequal 99° and 81°, respectively, is that it takes about 9° of opaque shutter rotation to totally block the photosensor beam for it to produce a signal state change which will ultimately result in a trigger signal being provided for causing an X-ray pulse. On the other hand, when the shutter leaves the beam, the photosensor responds as soon as any light falls on it. The output signals from photosensor 92 are indicated by a dashed line in FIG. 2 to be delivered to an input 96 of a switching and sync circuit 95 that is shown in FIG. 1 as will be discussed soon.

The means for commutating the X-ray pulses relative to angular positions of the filters and power line frequency is only exemplified herein by a shutter that chops a light beam. This is intended to be illustrative rather than limiting. For instance, slip ring segments on a rotationally adjustable insulting support cooperating with brushes could be used.

The photosensor output signal state changes are input to a switching and synchronizing circuit symbolized by the block marked 95 in FIG. 1. Input of this alternating signal is represented by the arrow-headed lined marked 96. A power line frequency reference signal is also provided as indicated by the arrow-headed line marked 97. Every time the shutter causes a signal state change to occur, the switching and sync circuit produces alternate output signals which are outputted on a cable 98 in FIG. 1 to an X-ray tube bias voltage source 99. The bias voltage source responds by changing the bias voltage on the X-ray tube in this particular example so the tube will produce a high energy X-ray pulse for one signal state and a low energy pulse for the other signal state. The bias voltage for the X-ray tube is supplied from the bias voltage source to the cathode, not shown, of the tube by way of a line 100. High voltage for applying to the anode, not shown, of the X-ray tube is supplied by way of a cable 101 from an X-ray transformer and a control module represented by the block marked 102. The pair of lines 103 for supplying the filament, not shown, of the X-ray tube are also represented schematically as running out of the X-ray transformer and control block 102. The sync circuit provides signals by way of line 105 to the CPU 21 so the CPU can detect whether data coming in from the X-ray detector via the data acquisition system relates to the image associated with a high energy or low energy X-ray pulse. An X-ray tube power supply for causing an X-ray tube to emit alternate low and high energy X-ray pulses is described in a co-pending application Ser. No. 208,095, filed Nov. 18, 1980, now U.S. Pat. No. 4,361,901, and assigned to the assignee of this application.

As mentioned briefly earlier in reference to FIG. 1, a high and a low energy X-ray pulse is provided for each slice of the body throughout the length of the scan. Thus, the data acquisition system 20 acquires separate sets of analog signals from X-ray detector 18 representative of X-ray attenuation of the fan-shaped X-ray beam for each pulse. This data is converted to digital data in the acquisition system and delivered to CPU 21. In reality the CPU has two memories for storing signals corresponding to the low and high energy X-ray pulses. For facilitating explanation, however, the memories are shown isolated in FIG. 1 and are marked memory 1 and memory 2. A line marked 106 symbolizes an address bus and a bidirectional data bus on which the X-ray attenuation data is exchanged with the CPU.

Every time the rotating shutter causes the switching and sync circuit 95 to initiate alternate high and low energy X-ray pulses, sync circuit 95 provides a signal to the CPU via bus 95 which causes the CPU to switch the attenuation data to memory 1 for the high energy pulse and to memory 2 for the low energy pulse. It is an important feature of the invention to, under selectable shutter control, set up for switching the data to alternate memories in advance of the start of the X-ray pulses. Moreover, as should now be clear, the rotational position of the filter drum represented by the positively related rotational position of the shutter results in state change signals being provided to the system electronics for switching the system in synchronism with the alternating energy X-ray pulses. Thus, the synchronizing problems which resulted from having the X-ray detector put out a signal to switch between memories, as in the prior art, are avoided.

Figure 8:
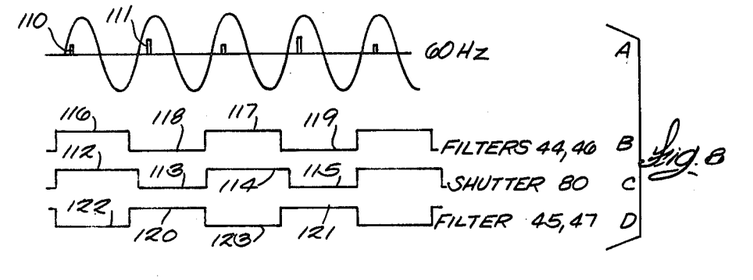
FIG. 8 consisting of parts A-D, is a timing diagram for explaining the functional features of the new filter device.

FIG. 8, comprised of parts A–D, is useful for explaining the time relationships between power line frequency, X-ray pulse occurrence, filter angular positions and shutter angular positions. Part A depicts the power line frequency waveform typified by 60 Hz. Occurrence of low and high energy X-ray pulses is indicated by pulses 110 and 111. Angular adjustment of the filter drum and shutter enables obtaining the X-ray pulses at any point along the half-cycles of the power line frequency. As illustrated, the X-ray pulses are being caused to occur at about 45° from each zero crossing of the sinusoidal waveform. By adjusting the angular position of the shutter they may be caused to occur at any selected point along the waveform.

Part C of FIG. 8 shows the timing of the rotating shutter blades. As the shutter blade rotates, one shutter blade may interrupt the light beam to the photosensitive device for the interval represented by that part of the waveform marked 112 at which time the output signal from the photosensitive device would be opposite or in its low state. In this design the device is dark for 99° of shutter rotation. When the shutter rotates beyond 99°, the light beam is not interrupted since the beam passes through a gap between blades for the interval represented by that part of the shutter blade timing diagram marked 113 and the output signal is again opposite or in its high state for 81°. When the shutter rotates beyond 81°, the other shutter blade is in the light beam for 99° as indicated by that part of the waveform which is marked 114 at which time the output signal from the photosensitive device is again in its low state. Further rotation disposes the gap between the shutter blades in the beam again for 81° as indicated by that part of the timing diagram which is marked 115. At this time, the output signal from the device goes high again. The switching and synchronizing circuit in FIG. 1 responds to these state changes with a little delay which would make the exact location at which the low and high energy X-ray pulses 110 and 111 occur somewhat unpredictable. However since the shutter can be adjusted angularly, it is adjusted so that the X-ray pulses occur along the 60 Hz waveform at exactly where they are wanted. Of course, each time a low or high energy X-ray pulse occurs, the synchronizing circuit 95 in FIG. 1 provides a signal to the CPU 21 so the CPU can differentiate between attenuation data signals that correspond to the respective low and high energy pulses to thereby produce data for two separate x-ray images.

Referring again to FIG. 8, it will be noted in part B that filter elements 44 and 46 are in the beam for the time intervals indicated by those parts of the timing diagram for the filters marked 116 and 117. When filters 44 and 46 are rotated out of the beam as indicated by those portions of their timing diagram marked 118 and 119, the other pair of filters 45 and 47 align with the beam as indicated by those parts of their timing diagram in part D marked 120 and 121. Filters 45 and 47 are out of the beam during those parts of their timing diagram marked 122 and 123. It will be evident in FIG. 8 that each pair of filters 44, 46 and 45, 47 are disposed across the X-ray beam path one time during each full cycle of the 60 Hz waveform and two times for every revolution of the filter drum. First one pair of diametrically opposite filter elements 44 and 46 are in the X-ray beam simultaneously. When the filter drum rotates another 90°, the next pair of filter elements 45 and 47 go into the beam. In another 90° of rotation, the first pair of filter elements 44 and 46 are again in the beam although the filter element which was on the top of the drum when the preceeding X-ray pulse occurred would now be on the bottom of the drum.

It will be evident in FIG. 8 that adjusting the shutter angle about its rotational axis in one direction or another amounts to shifting its timing diagram represented in part C of FIG. 8 to the right or left to adjust the phase relationship between the shutter and the 60 Hz power line frequency in part A and, as previously explained, this will establish the points along the power line sinusoidal waveform at which the low and high energy X-ray pulses will occur. Angular adjustment of the filter drum in one rotational direction or the other relative to the gear 59 and, hence, the motor shaft is tantamount to shifting the timing waveform for the filter elements where the thin fan-shaped beam will penetrate the elements upon occurrence of the X-ray pulses.

It will be evident from FIG. 8 that if the filter drum is rotating at 900 rpm or 15 rps and two pairs of filter elements are used on the spinning drum and the shutter has two blades and two gaps, one high energy and one low energy X-ray pulse can be provided for every 1/60th of a second or every full wave of the power line frequency. Thus, in this example, there are thirty low energy and thirty high energy X-ray pulses power second and the low and high energy pulses making a pair are 1/60th of a second or a little more than 16 ms apart. The X-ray pulse durations are typically in the range of 1 to 5 ms in the illustrated embodiment. Thus, there is likely to be little change in anatomical conditions between low and high energy pulses which means that there will be practically no blurring due to motion that accompanies beating of the heart or changes in the thorax dimensions due to breathing.

Those skilled in the art will recognize that the frequency of the low and high energy X-ray pulses could be increased or doubled if the number of shutter blades and gaps between them where doubled and if the number of filter element pairs were doubled. If these alterations were made one high energy and one low energy pulse could be provided every 1/60th of a second. However, this would mean that the X-ray detector 18 and the data acquisition system 20 would have to be capable of handling a set of attenuation data for each slice of the body every 1/120th of a second as opposed to every 1/60th of a second in the illustrative embodiment where the rotating shutter has two blades and two gaps and the filter wheel has two pairs of diametrically opposite filter elements. The speed of the data acquisition system and the minimum time for clearing the detector cells between X-ray pulses, therefore, is what may set the upper limit at which the X-ray pulses can be provided and, of course, it determines the minimum time between low and high energy pulses in a pair. In reality, however, to increase the frequency of filter placement in the X-ray beams, any even number of filter elements 44, 46 and 45, 47 could be used on the spinning drum or, as an alternative, the gear ratio between the ac motor 55 and the filter drum 40 can be changed.

Although a preferred embodiment of the new filter device has been described in detail, such description is intended to be illustrative rather than limiting and the true scope of the invention is to be determined only by construing the claims which follow.

We claim:

1. A device for filtering X-ray beam pulses at high and low energy levels projected alternately from an X-ray source toward a location for being occupied by a body, said device comprising:
   an axially extending hollow mounting member supported for rotation,
   first and seconds part of elements having different filtration properties mounted on said member at opposite sides, respectively, of its axis of rotation such that the X-ray beam will pass through both elements in a pair simultaneously when the elements are rotated across the X-ray beam,
   ac motor means for being energized at power line frequency and for running continuously concurrently with X-ray beam pulsing,
   a rotatable member for being driven rotationally by the motor means about an axis coinciding with the axis of said mounting member,
   coupling means interposed between said motor driven rotatable member and said mounting member, said coupling means being adjustable rotationally about said coinciding axes to a selected angular position for establishing the desired angular relationship of the elements with respect to the motor driven rotatable member, and
   means for controlling said X-ray source to project an X-ray beam pulse coordinately with said elements being rotated into the X-ray beam path.

2. The device defined in claim 1 wherein said means for controlling said X-ray source comprises:
   rotatable shutter means having circumferentially adjacent alternate light transmissive and light opaque regions, said shutter means being mounted to said driven rotatable member for being adjusted rotationally to a selected angular position about said coinciding axes of the mounting member and the driven rotatable member,
   a source of a light beam and a photosensitive device spaced therefrom for cooperating with said shutter means, and device providing one output signal state when the light from the source is interrupted and another output signal state when the light is restored, said shutter means rotating in the path of the light beam for said opaque regions and said transmissive regions to alternately interrupt and restore said light beam, respectively, occurrence of one signal state resulting in said X-ray source projecting a pulse at one energy and occurrence of the other signal state resulting in the X-ray source projecting a pulse at another energy.

3. The apparatus defined in claim 2 including:
   X-ray detector means responsive to intercepting the X-ray beams that pass through said elements simultaneously and a body by producing data representative of X-ray attenuation for the respective different energy X-ray pulses,
   first and second memories, and
   means responsive to occurrence of one state change by switching data corresponding to one of the X-ray energies to one memory and to occurrence of the next state change by switching data corresponding to another X-ray energy to the other memory.

4. The filtering device defined in claim 1 wherein:
   said coupling means between said motor driven rotatable member and said mounting member is composed of a part having a circular slot and screw means passing through said slot for enabling said rotational adjustment and for clamping said part to said motor driven rotatable member, said part having lug means projecting axially from it toward said mounting member,
   another part of said coupling means extending axially from said mounting member, said other part having a groove in which said lug means is engageable for driving said mounting member rotationally,
   a rotatable shaft to which said motor driven rotatable member is fastened, said shaft extending through each coupling part to thereby support the mounting member, said mounting member and said other coupling part being slidable on and off said shaft as a unit for installing and removing said mounting member, and
   means for supporting the end of the mounting member remote from the coupling for rotation and for maintaining said coupling parts in engagement.

5. The filtering device defined in claim 1 wherein:
   said motor driven rotatable member is a gear,
   a shaft mounted for rotation, said gear being fixed to said shaft, said motor having a shaft and a pinion fastened on said shaft, said pinion being engaged in driving relation with the gear, the second pair of elements being mounted to said mounting member, on opposite sides of its axis between the elements composing said first pair so that the same pair of elements will be in the X-ray beam for every 90 degrees of mounting member rotation, said means for controlling said X-ray source including shutter means mounted for rotational adjustment on said gear about the axis of the gear, said shutter means having diametrically opposite radially extending blade segments with gaps between them and including a light beam source and photosensitive means adjacent the rotating shutter means for producing a signal having one state when a shutter blade interrupts the beam and another state when a gap allows the beam to be restored, said state changes resulting in said X-ray source projecting respective high and low energy beams.

6. The device defined in claim 5 wherein the ratio of the gear to the pinion is 4 to 1 and the motor is operated at 3600 revolutions per minute and the power line frequency is 60 Hz.

7. A device for filtering X-ray beams in a system comprising an X-ray source, means for controlling said X-ray source to project alternate low and high energy pulsed X-ray beams, means for collimating said beams into a thin fan-shaped configuration and means for producing relative scanning movement between the X-ray source and a body being examined such that a high and a low energy beam can be projected through each layer in a succession of layers in the body, and detector means for producing signals corresponding to differential attenuation of the beams by the body layer during each energy pulse to enable reconstruction of projection images of the body region scanned, said device comprising:

hollow rotatable drum means, a first pair of filter elements mounted on said drum means diametrically opposite of each other and a second pair of filter elements having different filtration properties than the first pair mounted diametrically opposite of each other but displaced nominally 90° from the respective elements in the first pair, said elements having sufficient axial length for the fan-shaped beam to pass through them, an ac motor energized at power line frequency said motor having a shaft, means for driving said drum means in such manner that one pair of filters will be in the path of the low energy beam pulse when it is caused to occur and the other pair of filters will be in the path of the high energy pulse when it is caused to occur, said drum having means comprising a pinion fixed on said motor shaft, another shaft journaled for rotation and a gear fixed on the shaft, the pinion being meshed with the gear and the ratio of the gear to the pinion being 4 to 1, coupling means having one part mounted to said gear in a manner that permits angular adjustment of the part about the rotational axis of the gear, said coupling means having another part extending axially from the drum means, said parts being detachably interengaged, said other shaft extending through both parts to provide support for said drum means, shutter means having alternate circumferentially arranged light transmissive and light opaque regions, said shutter means being mounted on said gear for being adjusted to a selected angular position about the gear and drum means axes, a light source and photosensitive means, said shutter means being rotatable across the light beam path from the source to the photosensitive means, said means producing output signals state changes in response to said opaque and said light transmissive regions of the shutter being rotated alternately across the beam path, said means for controlling the X-ray source responding to occurrence of alternate signal states by causing said X-ray source to produce corresponding alternate high and low energy X-ray beam pulses.

8. The filter device as in claim 7 wherein said ac motor rotates at synchronous speed but has a phase shift relative to power line frequency due to loading and said shutter is adjusted on said gear such that the X-ray pulses, respectively, are caused to occur when the amplitude of the power line frequency waveform is increasing between zero and peak amplitude.

9. The filter device as in claim 7 wherein said motor rotates at 3600 rpm but has a phase shift relative to power line frequency, said power line frequency is 60 Hz, the ratio of the gear to the pinion is such that the filter element drum rotates at one-fourth of the motor speed, the shutter means is adjusted such that the X-ray pulses, respectively, are caused to occur when the amplitude of the power line frequency is increasing between zero and peak, and the coupling means between the gear and the filter element mounting drum is adjusted angularly so the filter elements will be in the X-ray beam path before an X-ray pulse having the energy for the corresponding filter is initiated.

10. The apparatus as in any of claims 7 or 8 including:
first and second memories,
means responsive to one state change by switching data representative of said signals that correspond to a high energy X-ray pulse to one memory and responsive to the next state change by switching data representative of said signals that correspond to a low energy X-ray pulse to the other memory.

11. The apparatus as in claim 7 including:
housing means for said rotatable filter drum means having opposed walls, one of the walls supporting a bearing in which said shaft that has the gear on it is journaled, the other opposite wall having an opening, a door member removably mounted on said opposite wall for closing said opening, bearing means mounted in said door member and a shaft extending axially from said filter drum means into the bearing means when said door member is mounted, removal of said door member allowing said detachably interengaged coupling means to be disengaged for removing the filter drum means from the housing.

* * * * *

UNITED STATES PATENT AND TRADEMARK OFFICE
CERTIFICATE OF CORRECTION

PATENT NO. : 4,399,550
DATED : August 16, 1983
INVENTOR(S) : Robert B. Hauck, Floyd L. Gray, Richard T. Brandt It is certified that error appears in the above—identified patent and that said Letters Patent is hereby corrected as shown below:

Claim 1, Column 11, Line 52, "first and seconds part of" should read --first and second pairs of--

Claim 2, Column 12, Line 17, "and" should be --said--

Signed and Sealed this

Fifteenth Day of November 1983

[SEAL]

Attest:

Attesting Officer

GERALD J. MOSSINGHOFF

Commissioner of Patents and Trademarks